United States Patent [19]

Bacskai

[11] 4,264,503
[45] Apr. 28, 1981

[54] POLYMERIZATION PROCESS USING A SODIUM CARBOXYLACTAMATE CATALYST

[75] Inventor: Robert Bacskai, Kensington, Calif.

[73] Assignee: Chevron Research Company, San Francisco, Calif.

[21] Appl. No.: 794,447

[22] Filed: May 6, 1977

Related U.S. Application Data

[63] Continuation of Ser. No. 588,997, Jun. 20, 1975, abandoned.

[51] Int. Cl.³ .................. C07D 207/12; C07D 211/40; C07D 222/10
[52] U.S. Cl. .......................... 260/326.2; 260/239 B; 260/239 BF; 260/239.3 R; 260/239.3 A; 260/326.5 FN; 546/243
[58] Field of Search ............. 260/78 P, 326.5 FN, 260/239.3 A, 239.3 R, 326.2, 239 BF, 239 B; 546/243

[56] References Cited

U.S. PATENT DOCUMENTS

| | | | |
|---|---|---|---|
| 3,075,953 | 1/1963 | Carlson et al. | 260/78 P |
| 3,346,566 | 10/1967 | Chiddek et al. | 260/78 P |
| 3,681,293 | 8/1972 | Jarovitsky et al. | 260/78 P |
| 3,681,295 | 8/1972 | Jarovitsky | 260/78 P |
| 3,682,869 | 8/1972 | Jarovitsky | 260/78 P |
| 3,721,652 | 3/1973 | Barnes | 260/78 P |
| 3,793,258 | 2/1974 | Reinking et al. | 260/78 P |
| 3,835,100 | 9/1974 | Sekiguchi et al. | 260/78 P |
| 3,945,897 | 3/1976 | Choi | 260/78 P |
| 3,968,087 | 7/1976 | Choi | 260/78 P |

*Primary Examiner*—Mary C. Lee
*Attorney, Agent, or Firm*—D. A. Newell; T. G. DeJonghe; L. S. Squires

[57] ABSTRACT

The polymerization of 2-pyrrolidone is achieved in high yield in the presence of a sodium-derived catalyst activator produced by the reaction of carbon dioxide with the sodium lactamate derived from the reaction of a sodium alkoxide and a 5–7 membered-ring lactam in an inert liquid nonsolvent.

2 Claims, No Drawings

POLYMERIZATION PROCESS USING A SODIUM CARBOXYLACTAMATE CATALYST

This application is a continuation of application Ser. No. 588,997, filed June 20, 1975, now abandoned.

BACKGROUND OF THE INVENTION

1. Field of the Invention

Poly-2-pyrrolidone (also known as nylon-4) is a polymer composed of repeating structural units of the formula

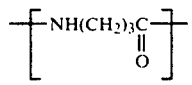

The polymer is produced by alkaline-catalyzed polymerization of 2-pyrrolidone, preferably in the presence of a catalyst comprising the reaction product of a 5–7 membered-ring lactamate of an alkali or alkaline earth metal and carbon dioxide, e.g., the reaction product of potassium pyrrolidonate and carbon dioxide. This reaction product, which for example may be called "potassium carboxypyrrolidonate" or the "adduct of carbon dioxide and potassium pyrrolidonate", is believed to function as an initiator or activator of polymerization. In whatever manner the metal carboxylactamate may function, there is no known reason, nor any reason suggested in the literature, why the choice of a particular metallic counterion for the catalyst should effect the degree of conversion achieved in the polymerization of 2-pyrrolidone. Yet it is observed that $CO_2$-containing catalysts derived from sodium compounds consistently yield substantially lower conversions than $CO_2$-containing catalysts derived from potassium compounds under identical polymerization conditions. Generally, polypyrrolidone molecular weights determined by viscosity measurements are also substantially lower for sodium-derived catalysts than for potassium-derived catalysts under identical conditions.

There are substantial economic advantages to the use of sodium-derived catalysts over the use of potassium-derived and other catalysts under the same processing conditions. All other factors being equal, the use of sodium would be preferred for that reason alone. The only problem is that the degree of conversion of monomer to polypyrrolidone and molecular weight of polypyrrolidone achieved with sodium-derived catalysts has heretofore been so inferior as to present no real alternative to other catalyst systems.

2. Description of the Prior Art

U.S. Pat. No. 3,346,566 discloses the polymerization of 2-pyrrolidone in the presence of a catalyst produced by reacting an alkali metal alkoxide, or alkaline earth metal alkoxide, with a 5–7 membered-ring lactam and removing the alcohol released from the alkoxide either by distillation during the reaction, or by recovery of the product metal lactamate as a filterable solid after the reaction.

U.S. Pat. No. 3,721,652 discloses the polymerization of 2-pyrrolidone under conditions of alkaline catalysis in the presence of carbon dioxide. It further teaches that the alkaline catalyst, sodium pyrrolidonate, reacts with carbon dioxide to form an adduct which may be separated by precipitation from its benzene solution.

In general, the prior art teaches the interchangeable use of 2-pyrrolidone polymerization catalysts derived from Group I (alkali metal) compounds, and, in particular, does not provide a reasoned distinction between sodium- and potassium-derived catalysts in the $CO_2$-initiated polymerization of 2-pyrrolidone.

U.S. Pat. No. 3,835,100 (Cols. 1 and 9) teaches that alkali metal pyrrolidonate catalysts are difficult or impossible to purify and furthermore, lose catalytic activity with time.

SUMMARY OF THE INVENTION

The process of preparing a high-yield sodium-derived catalyst activator for the polymerization of 2-pyrrolidone comprises the steps of forming a sodium lactamate by heating at about reflux temperature a $C_1$–$C_5$ sodium alkoxide with a 5–7 membered-ring lactam in the presence of an inert liquid nonsolvent for said sodium lactamate, contacting said sodium lactamate with carbon dioxide, and recovering the product sodium carboxylactamate.

DESCRIPTION OF PREFERRED EMBODIMENTS

A process has now been found for producing a sodium-derived catalyst system which can be used to prepare a polymer of 2-pyrrolidone in high yield. In the polymerization process of the present invention, 2-pyrrolidone is polymerized at a temperature of from about 15° C. to about 100° C. for a period from about 4 to about 100 hours in the presence of a catalyst system comprising a sodium carboxylactamate such as sodium carboxypyrrolidonate. Specifically, the sodium carboxylactamate is produced by a process including the steps of first forming a sodium lactamate by heating at about reflux temperature a $C_1$–$C_5$ sodium alkoxide with a 5–7 membered-ring lactam in the presence of a inert liquid nonsolvent for the sodium lactamate, contacting the sodium lactamate with $CO_2$, and recovering the product sodium carboxylactamate.

Sodium Alkoxide

The alkoxide which finds use within the scope of the present invention is a dry sodium alkoxide of from 1 to about 5 carbon atoms. The sodium alkoxide is made, for example, as described in U.S. Pat. No. 3,346,566, by heating sodium dispersed in a dry inert liquid suspending agent, such as benzene, with an equivalent amount of a primary, secondary or tertiary aliphatic alcohol of from 1 to about 5 carbon atoms. These alkoxides include sodium methoxide, sodium ethoxide, sodium n-butoxide, sodium t-butoxide, sodium isopropoxide, sodium isobutoxide, sodium n-pentoxide, sodium isopentoxide, sodium t-pentoxide, etc. Of these, the preferred alkoxides are those whose corresponding alcohols form an azeotrope with an inert liquid nonsolvent for sodium lactamate, e.g., especially preferred is sodium methoxide, whose corresponding alcohol, methanol, forms an azeotrope with the sodium pyrrolidonate-nonsolvent, benzene.

Sodium Lactamate

The sodium lactamate is prepared by heating at about reflux temperature the alkoxide and a stochiometric equivalent amount of a 5–7 membered-ring lactam in the presence of an inert liquid nonsolvent for the sodium lactamate. The reflux temperature is, of course, the reflux temperature of the inert liquid nonsolvent. The inert liquid nonsolvent is preferably selected from among lower aliphatic hydrocarbons and lower monocyclic aromatic hydrocarbons containing at least about 5 carbon atoms.

The inert liquid nonsolvent is provided as a reaction medium and aid to the separation of sodium lactamate. Its character and nature is immaterial so long as it is unreactive towards sodium lactamate, sodium alkoxide, and carbon dioxide under reaction conditions; it is a liquid having a boiling point in the range of about 30°–200° C.; and it is a nonsolvent for sodium lactamate. The amount of nonsolvent used is not critical. Any amount which provides a workable slurry, or dispersion, for the sodium lactamate product will suffice. Examples of such inert liquid nonsolvents include lower monocyclic aromatic hydrocarbons such as benzene, toluene and xylene; alkanes which are liquid at about 25° C., such as pentane, hexane, octane, and cyclohexane; and ethers and ketones, such as di-n-propyl ether, tetrahydrofuran, dioxane and so forth. Of these, the preferred inert liquid nonsolvents are those which are completely miscible with 2-pyrrolidone at temperatures above 25° C., and the most preferred are those which form an azeotrope with the alcohol generated by the reaction of sodium alkoxide with the lactam. The inert liquid nonsolvent is dry, i.e., substantially free of water.

The lactam finding use in the process of the present invention is a 5-, 6- or 7-membered ring amide including C-alkyl substituted lactams. Such lactams embrace 2-pyrrolidone, piperidone and caprolactam, including $C_1$–$C_5$ alkyl-substituted 2-pyrrolidone, piperidone and caprolactam other than N-alkyl-substituted lactams such as N-methyl-2-pyrrolidone. The preferred lactam for the production of catalyst for the polymerization of 2-pyrrolidone is 2-pyrrolidone.

In one embodiment of the invention, while the reaction between the sodium alkoxide and the lactam proceeds with heating under reflux conditions, the alcohol generated from the alkoxide-lactam reaction is removed from the reaction mixture by distillation as the alcohol or as an azeotrope with the inert nonsolvent. Alternatively, the alcohol may be removed by distillation after the reaction is completed as the alcohol, or as an azeotrope with the inert nonsolvent. In another embodiment of this invention, the alcohol is removed from the sodium lactamate product by filtration after the reaction. The reaction proceeds for about 0.1 to about 6 hours at temperatures from about 30° C. to about 200° C., preferably from about 40° C. to about 200° C. (see U.S. Pat. No. 3,346,566). The sodium lactamate product is obtained as a slurry, or dispersion, in the inert liquid nonsolvent. The sodium lactamate so obtained may be used directly in the subsequent reaction with carbon dioxide; or first it may be separated by filtration, purified by successive washings in an inert liquid nonsolvent such as benzene or pentane and dried by conventional means, or it may be purified by recrystallization from a solvent, or other purification procedures known to the art.

In a cyclical process embodiment of the present invention, the alcohol removed from the reaction of sodium alkoxide with lactam is subsequently reacted with sodium metal to regenerate the sodium alkoxide, which is then recycled to the lactam-alkoxide reaction zone, with or without further treatment and addition of make-up quantities of nonsolvent.

In a preferred embodiment, the alcohol is removed from the alkoxide-lactam reaction zone as an azeotrope of the inert liquid nonsolvent, the azeotrope essentially forms the reaction medium for the subsequent reaction of the alcohol with sodium metal, and the slurry or dispersion of the product sodium alkoxide in the inert nonsolvent is recycled to the alkoxide-lactam reaction zone.

Sodium Carboxylactamate

The product-of-the-process which I term "sodium carboxylactamate" is an adduct of carbon dioxide and sodium lactamate of unknown structure. It may be a sodium-N-carboxy-2-lactamate or have another structure. In particular, it is not established, nor is it intended to imply, that carbon dioxide and sodium lactamate necessarily form an adduct in 1:1 molecular ratio.

In the reaction of sodium lactamate with carbon dioxide, the sodium lactamate is preferably in the form of a slurry or dispersion, in the inert liquid nonsolvent e.g. sodium carboxypyrrolidonate is produced by contacting carbon dioxide with a slurry of sodium pyrrolidonate in benzene. The sodium carboxylactamate is also insoluble in the inert liquid nonsolvent and is separated by filtration, centrifugation, etc. The sodium carboxylactamate may be used directly as separated, or purified as described for the sodium lactamate.

The amount of carbon dioxide added to the sodium lactamate may be an equivalent amount (1:1 mol ratio $CO_2$:sodium) or less than an equivalent amount. If less than an equivalent amount of $CO_2$ is used, the product is a mixture of sodium carboxylactamate and sodium lactamate, which is the usual catalyst system of this invention for 2-pyrrolidone polymerization. About 0.1–0.9 mols carbon dioxide per mol sodium lactamate is reacted with sodium lactamate to form a catalyst system of about 10–90 mol percent sodium carboxylactamate and 90–10 mol percent sodium lactamate, based on total lactamate (carboxylactamate plus lactamate). Preferably, the catalyst system will contain sodium and carbon dioxide in the mol ratio $Na:CO_2 = 0.2$–$0.7$. When an equivalent amount or excess carbon dioxide is added to the sodium lactamate the product is substantially entirely sodium carboxylactamate. For use in polymerization, the carboxylactamate is used with 90–10 mol percent sodium lactamate to make the desired catalyst system. Most preferably the catalyst system comprises about 65–40 mol percent sodium lactamate and about 35–60 mol percent sodium carboxylactamate.

Conditions for the addition of carbon dioxide to sodium lactamate consist of contacting with gaseous carbon dioxide the sodium lactamate at a temperature of from about 5° C. to about 130° C. Surprisingly, the gaseous carbon dioxide is found to react readily with the slurry of solid sodium lactamate to produce the desired sodium carboxylactamate. Heretofore, carbon dioxide has been added to the solution of sodium lactamate in the lactam to produce the sodium carboxylactamate.

While the embodiments of the present invention have been related in terms of the addition of carbon dioxide to sodium lactamate to form sodium carboxylactamate, they could have been related in terms of the addition of sulfur dioxide (or other compounds termed "activators" or "initiators" for the polymerization of 2-pyrrolidone which form adducts with sodium lactamate, and which function as co-catalysts for the polymerization of 2-pyrrolidone) to sodium lactamate in the same amounts and under the same conditions to form sodium sulfoxylactamate, which is also an activator for the polymerization of 2-pyrrolidone. In addition to sulfur dioxide, which is substitutional in whole or part for carbon dioxide, other compounds which are believed to be directly substitutional for carbon dioxide in whole or part in this process include COS, and NO₂, as well as compounds which release CO₂ or SO₂ under the ambient alkaline conditions of this process.

Polymerization Conditions

The process of this invention is specifically applicable to the polymerization of 2-pyrrolidone to form a polymeric carbonamide of relatively high molecular weight which has recurring amide groups separated by a trimethylene radical as an integral part of the main polymer chain. This polymer is capable of being formed into filaments having substantial orientation along the filamentary axis, high tensile strength, and other properties suitable for making into textiles. It can be made into filaments, shaped articles and films by melt spinning, molding and extruding.

In order to produce high-quality poly-2-pyrrolidone capable of being formed into fibers, filaments and yarn of commercial textile quality, it is necessary that the 2-pyrrolidone monomer be of high purity. Depending upon the process of manufacture, commercially available 2-pyrrolidone may contain appreciable amounts of various impurities, some of which are believed to interfere deleteriously with polymerization. Purification of the monomer to polymerization grade is achieved by crystallization; distillation; distillation from a boron oxide, as disclosed in U.S. Pat. No. 3,806,427; aqueous caustic hydrolysis and distillation, as disclosed in U.S. Pat. No. 3,721,652; acid treatment and distillation, as disclosed in U.S. Pat. No. 3,721,652; and these and other purification techniques in combination.

The process of the present invention is just as applicable to the production of polymers of C-alkyl substituted pyrrolidone, such as 4-methyl-2-pyrrolidone, and copolymers of 2-pyrrolidone, such as with caprolactam, as to the production of poly-2-pyrrolidone. Consequently, in general, and unless otherwise indicated, the words "monomer" and "2-pyrrolidone" are interchangeable, and "monomer" denotes 2-pyrrolidone, substituted 2-pyrrolidone, and any compound capable of copolymerizing with 2-pyrrolidone under the stated conditions of alkaline polymerization catalysis.

The components of the polymerization catalyst system, comprising an alkaline catalyst and sodium carboxylactamate, may be brought together and added to the monomer in any way known to the art of polymerization. The alkaline catalyst is also available as a solid, and the catalyst system may be made by mixing the solid components followed by the addition to monomer, or the two components may be added separately to the 2-pyrrolidone, or the solid sodium carboxylactamate may be added to 2-pyrrolidone containing alkaline catalyst previously made by any in situ method. Such alkaline catalysts are selected from those disclosed in the prior art, e.g., sodium lactamate, potassium lactamate, quaternary ammonium lactamate, sodium or potassium pyrrolidonate, etc. Initiators or activators such as acyl derivatives, U.S. Pat. Nos. 2,739,959; N-acyl lactams, 2,809,958; oxides of Group VI such as SO₂, 3,174,951; halides and oxyhalides, halosilanes, CS₂, amides, sulfoamides, isocyanates, NO₂, carbonyl halides, etc., may also be added to the polymerizate in amounts sufficient to effect substantial conversion and reasonable yields of high-viscosity polymer in a reasonable period of time. Normally, such initiators are added in amounts of about 0.01-0.2 mol percent, base on total monomer.

The total polymerization catalyst system comprises from about 0.5 to 30 mol percent, or higher, of the monomer-catalyst mixture (the polymerizate), based on total monomer. Preferably about 5-20 percent based on total monomer and most preferably about 10 mol percent, of the catalyst system is used. In itself, the sodium carboxylactamate comprises up to a major portion of the total polymerization catalyst system. Preferably 20-70 mol percent, and most preferably 35-60 mol percent of the catalyst system consists of sodium carboxylactamate. Total monomer consists of 2-pyrrolidonate catalyst, including sodium carboxypyrrolidonate, 2-pyrrolidone provided as solvent for said catalyst, and any additional monomer charged to the reactor for polymerization reaction. The total polymerization catalyst system comprises sodium carboxylactamate and alkaline catalyst such as as sodium pyrrolidonate, potassium pyrrolidonate, or quaternary ammonium lactamate.

In a preferred embodiment of the polymerization process of this invention, the polymerizate containing sodium carboxylactamate is heated to a temperature of about 80°-120° C. for a period of from about 0.05 to about 3 hours, preferably about 0.1-2 hours, before cooling to a preferred polymerization temperature at about 25° C.-70° C., and maintaining said preferred polymerization temperature for a period of about 4 to about 100 hours to effect polymerization. This thermal treatment of the polymerization is found to improve the yield. Alternatively, or additionally, the catalyst system may be isolated and stored under anhydrous conditions for an extended period, e.g., 10-20 days or longer, to achieve the increase in yield produced by the shorter thermal treatment. This increase in yield is not believed to be caused by dehydration.

In general, 2-pyrrolidone may be polymerized at a temperature of from about 15° C. to about 100° C., preferably 25° C. to 70° C., and most preferably from about 40° C. to about 60° C., under a pressure ranging from subatmospheric to superatmospheric, in the presence of a polymerization catalyst system for a period of from about 4 to about 100 hours or longer, preferably from about 8 to about 72 hours, more preferably from about 8 to about 48 hours. In continuous operation, polymerization time refers to average residence under polymerization conditions. Substantially anhydrous polymerization conditions are preferred; i.e., a slight amount of water, not exceeding about 0.1-0.2% by weight, based on total monomer, is permissible in the reaction mixture, but less than 0.1 weight percent water is preferred.

The product of the normal process of this invention is a solid polymeric material, polypyrrolidone. The product is obtained as a particulate solid or a comminutable solid product. Product whitness, polymer viscosity and melt spinnability (U.S. Pat. No. 3,721,652) are also important considerations in the choice of preferred process parameters.

Preparation of polymers of 2-pyrrolidone, according to the novel process of this invention, can be carried out with various amounts of monomers, catalysts, inert nonsolvent liquids, initiators and other additives—the amount of each being properly coordinated to produce the most effective polymerization. Although the preferred amounts of the components in the reaction have been given, it is to be understood that these are not intended to be limitations to polymerization, since it may be possible to effect substantial polymerization outside the preferred ranges.

EXEMPLIFICATION

The polymerization catalyst system for producing nylon-4 from 2-pyrrolidone using carbon dioxide activation has generally consisted of potassium carboxypyrrolidonate and potassium pyrrolidonate rather than the less expensive sodium salts. Both sodium and potassium salts are taught as being equivalent in this polymerization process (see U.S. Pat. No. 3,721,652, Col. 3, lines 5–6). Yet, in comparative experiments, better results, i.e., greater conversions of monomer and higher-molecular-weight polymers, are obtained using potassium-derived catalyst systems than are obtained using sodium-derived catalyst systems.

Under the presumption that unknown factors which deleteriously affect polymerization may be present in, or may be formed in, the production of the catalyst from sodium compounds, the sodium catalyst system has been separated, i.e., as the solid sodium carboxypyrrolidonate, and as the solid sodium pyrrolidonate, and purified, to no avail.

Examples 1–5 illustrate the preparation of catalyst systems from potassium compounds and their use in the polymerization of 2-pyrrolidone.

Polymer viscosity is measured at room temperature (about 25° C.) on the Gardener Viscosity Scale using a Gardner-Holdt Bubble Viscometer. 0.5 g of polymer is dissolved in 10 ml of concentrated formic acid (90% by weight HCOOH, 10% water). The polymer solution is compared in viscosity to the Gardener Bubble Standards, e.g., Standard U corresponds to 6.27 stokes, Standard Z corresponds to 22.7 stokes ("Physical and Chemical Examination, Paints, Varnishes, Lacquers and Colors" by H. A. Gardner and G. G. Sward, 12th Ed., 1962, distributed by Gardner Laboratory Company, Inc., Bethesda, Maryland).

EXAMPLE 1

200 g of 2-pyrrolidone (2.35 mols) distilled from dilute $H_2SO_4$ solution was contacted with 15.5 g of KOH pellets (0.24 mol, 86.2% KOH) in a stirred vessel and the mixture heated to incipient distillation over a period of about 16 minutes under reduced pressure, at a pot temperature (liquid temperature of about 120° C. The mixture was cooled to 30° C. and a calibrated amount of $CO_2$ was introduced to produce a catalyst system comprising potassium carboxypyrrolidonate and potassium pyrrolidonate in 2-pyrrolidone. The solution contained 30 mol percent potassium carboxypyrrolidonate based on total catalyst (3 mol percent on total monomer). The mixture was divided into 2 parts and poured into separate polyethylene bottles. The samples were each polymerized at 50° C. for 22 hours. The bottle contents, a hard polymeric mass, were comminuted, washed with water, and dried in vacuo. One sample showed a monomer conversion of 49.19% and a Gardner viscosity of $Z_2$, and the other sample showed a monomer conversion of 48.6% and a Gardner viscosity of $Z_2$.

EXAMPLE 2

Potassium carboxypyrrolidonate was prepared by contacting 55 g of purified 2-pyrrolidone with 5 g of KOH pellets (85.2% KOH) in a stirred vessel and heating the mixture to incipient distillation under reduced pressure for 13 minutes at a pot temperature of 118° C. The mixture was cooled to 35° C. and the vacuum replaced with nitrogen. About 125 ml of dry benzene was added to the mixture and $CO_2$ was bubbled through the mixture for 25 minutes. The clear benzene solution turned cloudy and a precipitate formed. The filtered, benzene-washed and dried precipitate, potassium carboxypyrrolidonate, weighed 12.71 g and had a nitrogen content of 7.82% (theory, 8.37%).

Polymerization of 2-pyrrolidone was effected by contacting 48.5 g of purified monomer with 2.71 g of KOH pellets (85.2% KOH), heating the mixture to incipient distillation under reduced pressure of about 1.5 mm Hg for 9 minutes at a pot temperature (liquid temperature) of about 105° C. and a head temperature (vapor temperature) of about 90° C., cooling the mixture to 30° C. and pouring it into a polyethylene bottle containing 2.94 g of isolated potassium carboxypyrrolidonate made as described above. The polymerizate was shaken to aid in dissolving the potassium carboxypyrrolidonate. It was then heated at 50° C. for 22 hours. The hard polymeric mass was chopped, washed with water and dried in vacuo at 70° C. The percent monomer conversion was 53.3% and the polymer had a Gardner viscosity of $Z_1$.

EXAMPLE 3

In this example the polymerization of 2-pyrrolidone is catalyzed by a catalyst system consisting of isolated potassium pyrrolidonate plus isolated potassium carboxypyrrolidonate made from metallic potassium.

Potassium metal (9.47 g, 0.24 mol) was added over a 5-hour period to a mixture of 150 ml of benzene and 25% mol excess 2-pyrrolidone. Only a trace amount of potassium remained undissolved. The product was filtered and washed with benzene, hexane and ether. 31.33 g of potassium pyrrolidonate, a hygroscopic white powder, was obtained. The product was dried and stored in a dessicator at room temperature. In a separate preparation, potassium carboxypyrrolidonate was prepared by adding 9.77 g of potassium metal to a 24% molar excess of 2-pyrrolidone in 170 ml of benzene over a period of 4 hours at 40°–51° C., distilling off 27 ml of benzene, cooling to 30° C. and bubbling in $CO_2$ for 25 minutes. The product was filtered, washed with benzene, hexane and ether, and dried. The yield was 35.76 g of a hygroscopic white powder, comprising potassium carboxypyrrolidonate (45.1 mol percent) and potassium pyrrolidonate (54.9 mol percent as calculated from $CO_2$ uptake).

To achieve polymerization of 2-pyrrolidone, 45 g of purified monomer was mixed in a dry box with 2.47 g of the isolated potassium pyrrolidonate and 5.52 g of the isolated potassium pyrrolidonate/potassium carboxypyrrolidonate by pouring the monomer into a polyethylene bottle containing these salts. The resulting mixture was heated for 22 hours at 50° C., yielding 24.03 g of polymer, corresponding to 49.26% conversion of monomer, and the polymer had a Gardner viscosity of X-Y.

EXAMPLE 4

A polymerizate having the same composition as in Example 3, i.e., 45 g of purified monomer, 2.47 g of potassium pyrrolidonate and 5.52 g of the potassium pyrrolidonate/carboxypyrrolidonate mixture, was subjected to heating under reduced pressure to incipient distillation before polymerization. The catalyst was weighed out in a dry box and mixed with monomer in a flask under nitrogen. The resulting mixture was heated to incipient distillation under reduced pressure of about 2.5 mm Hg at a head temperature of 90° C. and a pot temperature of 115° C. for 9 minutes. The mixture was cooled to 30° C. and the solution was poured into a polyethylene bottle which was then heated at 50° C. for 22 hours. The hard polymer product was worked up as usual, yielding 25 g of polymer corresponding to 55.35% conversion of monomer and having a Gardner viscosity of X-Y.

EXAMPLE 5

In this experiment, 24% of the monomer was distilled from the polymerizate before polymerization.

55 g of monomer was mixed in a flask under nitrogen with 2.47 g of potassium pyrrolidonate and 5.22 g of the potassium pyrrolidonate/carboxypyrrolidonate mixture of Example 3. The resulting mixture was heated under reduced pressure of 3.5 mm Hg, at a head temperature of 100° C. and a pot temperature of 118° C. to distill off 12.91 g of 2-pyrrolidone. The mixture was cooled to 30° C., poured into a polyethylene bottle and heated at 50° C. for 22 hours. The hard polymeric product was worked up in the usual way, yielding 22.66 g of polymer corresponding to 56.93% monomer conversion and having a Gardner viscosity of X-Y.

Example 6-10 illustrate the preparation of catalyst systems from sodium compounds other than sodium alkoxide and the use of these sodium-derived catalyst systems in the polymerization of 2-pyrrolidone.

EXAMPLE 6

This example illustrates polymerization of 2-pyrrolidone using a catalyst derived from sodium hydroxide and carbon dioxide.

50 g of purified monomer (0.587 mol) was contacted with 2.36 g of sodium hydroxide (0.059 mol, 98.2%) and heated at 106° C. under reduced pressure of 2.5 mm Hg for 29 minutes to dissolve the sodium hydroxide. The clear solution was heated to incipient distillation in 7 minutes at a pot temperature of 115° C. under reduced pressure of 2.5 mm Hg and a head temperature of 80° C. The mixture was cooled to 30° C. and a calibrated amount of $CO_2$ was added, such that the polymerizate was 7 mol percent sodium pyrrolidonate, and 3 mol percent sodium carboxypyrrolidonate, based on total monomer. The polymerizate was poured into a polyethylene flask and heated at 50° C. for 22 hours. The hard, solid polymer was chopped up, washed with water and dried in vacuo at 70° C. The yield was 15.14 g of polymer (35.26% conversion of monomer), having a Gardner viscosity of U-V.

EXAMPLE 7

This example illustrates the polymerization of 2-pyrrolidone using a catalyst consisting of isolated sodium pyrrolidonate and isolated sodium carboxypyrrolidonate made from sodium metal.

The sodium pyrrolidonate was made by contacting 14.37 g of a 40% sodium dispersion in mineral oil (0.25 mol Na), with 23.45 g of purified monomer in 125 ml of benzene. The sodium dispersion was added over a period of 1.5 hours at 40°-59° C. The product was diluted with 100 ml of benzene, filtered and washed with benzene, hexane and ether to give 24.33 g of product. It was dried at room temperature and stored in a dessicator. In a separate preparation, sodium pyrrolidonate was prepared as in the foregoing. Then carbon dioxide was added over a period of 19 minutes, during which the temperature rose from 30° to 47° C. The product, a mixture of sodium pyrrolidonate and sodium carboxypyrrolidonate weighing 31.72 g, was washed with benzene, hexane and ether, and dried in a dessicator.

To achieve polymerization, 5.03 g of the sodium pyrrolidonate and 2.03 g of the sodium pyrrolidonate/sodium carboxypyrrolidonate mixture was weighed out in a dry box and mixed in a polyethylene bottle with 45 g of purified monomer. After 22 hours at 50° C. the product was found to be soft, and contained only 0.06 g of polymer, corresponding to 0.12% conversion of monomer.

EXAMPLE 8

In this example the polymerizate of Example 7 was heated to incipient distillation before polymerization.

A polymerizate identical to that of Example 7 was heated to incipient distillation under reduced pressure and cooled to 30° C. before being poured into a polyethylene bottle and held at 50° C. for 22 hours. The product was found to be soft and contained only 1.88 g of polymer, corresponding to a monomer conversion of 4.23%, and the polymer had a Gardner viscosity less than A.

EXAMPLE 9

A polymerizate, made up as in Example 7 but containing 55 g of purified monomer, was heated under reduced pressure to distill off 9.12 g (16.4%) at a pot temperature of 118° C. and a head temperature and pressure of 92° C./2 mm Hg. The polymerizate was then poured into a polyethylene bottle and polymerized for 22 hours at 50° C. The yield was 3.84 g of polymer having a viscosity on the Gardner Scale of less than A and corresponding to 8.38% conversion of monomer.

EXAMPLE 10

This example illustrates the polymerization of 2-pyrrolidone with a catalyst made from sodium metal and $CO_2$.

1.39 g (0.059 mol) of sodium metal was added in small portions at 38°-45° C. over a period of 5.5 hours. A calibrated amount of $CO_2$ was added to give a polymerizate containing 7 mol percent sodium pyrrolidonate and 3 mol percent sodium carboxypyrrolidonate, based on total monomer. The polymerizate was poured into a polyethylene bottle and polymerized for 22 hours at 50° C. The product remained very soft, but was given the usual workup. 0.15 g of polymer was obtained, corresponding to a monomer conversion of 0.35%.

Examples 11-17 illustrate the preparation of catalyst systems from sodium alkoxide and their use in the polymerization of 2-pyrrolidone.

EXAMPLE 11

This example illustrates the preparation of sodium lactamate from the sodium alkoxide and the removal of the alcohol generated from the alkoxide by azeotropic distillation.

To 200 ml of benzene was added 21.6 g of sodium methoxide (0.4 mol). Distillation of benzene was begun (pot temperature 80° C., head 78° C.) and continued with addition of 37.45 g of purified 2-pyrrolidone (0.44 mol) over 24 minutes (head temperature dropped to 60° C. as the distillate contained methanol). Distillation continued until no more methanol was in the distillate and the head temperature returned to 78° C. Altogether, 148 ml was distilled out and 70 ml of benzene was added to replace it. The mixture was cooled to room temperature, filtered, washed with benzene and dried in vacuo at 84° C. The yield of sodium pyrrolidonate was 41.17 g.

In a separate preparation, sodium pyrrolidonate was produced from sodium methoxide as described, but before the sodium pyrrolidonate was isolated, $CO_2$ was bubbled into the mixture for 20 minutes, producing an exothermic reaction which raised the temperature to 40° C. The product was filtered, washed with benzene and dried at 22° C. in vacuo. The yield was 47.33 g of a solid product which was analyzed for nitrogen (10.64% by weight and sodium (17.76% by weight). These percentages indicate that the product had a Na:$CO_2$ mol ratio of about 1:0.5, corresponding to a mixture of about 50 mol percent sodium pyrrolidonate and about 50 mol percent sodium carboxypyrrolidonate. This mixture was used as the catalyst system where referred to in subsequent examples.

EXAMPLE 12

Polymerization of 2-pyrrolidone is herein illustrated with isolated sodium pyrrolidonate and isolated sodium carboxypyrrolidonate derived from sodium methoxide. 45 g of purified monomer was weighed into a polyethylene bottle in a dry box, then 6.8 g of the catalyst system of Example 11 was added. The polymerizate consisted of 90 mol percent 2-pyrrolidone and 10 mol percent of a catalyst system consisting of 5 mol percent sodium carboxypyrrolidonate and 5 mol percent sodium pyrrolidonate, i.e., 10 mol percent sodium pyrrolidonate and 5 mol percent carbon dioxide, based on total 2-pyrrolidone. The mixture was polyermized for 22 hours at 50° C. and the hard polymer was worked up in the usual way. The yield was 19.37 g of polymer, corresponding to 40.8% monomer conversion, and the polymer had a Gardner viscosity of X-Y.

EXAMPLE 13

This example illustrates the polymerization of 2-pyrrolidone with a sodium alkoxide-derived catalyst system and heating of the polymerizate to incipient distillation before polymerization.

Example 12 was repeated, except that before polymerization at 50° C. for 22 hours, the polymerizate was heated to incipient distillation under reduced pressure and then cooled to 30° C. The product waas a hard polymer which, when worked up in the normal way, yielded 12.3 g of polymer having a Gardner viscosity of X-Y, corresponding to 60.29% monomer conversion.

EXAMPLE 14

This example illustrates the use of an aged sodium alkoxide-derived catalyst system.

Example 12 was repeated, using the catalyst system of Example 11 after it has been stored in a dry box for 1 week. 6.8 g of the catalyst was then mixed with 45 g of purified monomer and polymerized as in Example 12. The yield was 19.08 g of a polymer having a Gardner viscosity of Y, corresponding to 39.6% monomer conversion.

EXAMPLE 15

Example 14 was repeated, using the same catalyst system, but the polymerizate was heated to incipient distillation under reduced pressure and cooled to 30° C. before being poured into a polyethylene bottle and polymerized at 50° C. for 22 hours. The product was a hard polymer, which was worked up as usual to yield a polymer having a Gardner viscosity of Y-Z and corresponding to 60.3% monomer conversion.

EXAMPLE 16

After 15 days' dry storage, 1.7 g of the catalyst system of Example 11 was mixed with 11.25 g of purified monomer in a polyethylene bottle and polymerized for 22 hours at 50° C. The hard polymer was worked up as usual, yielding 6.6 g of polymer having a Gardner viscosity of Y-Z, corresponding to 53.76% monomer conversion.

EXAMPLE 17

Example 16 was repeated, using 22.5 g of purified monomer and 3.4 g of the 15-day-old catalyst system of Example 11, mixed in a 100-ml flask. The mixture was stirred in a nitrogen stream at 100° C. for 17 minutes, during which the catalyst dissolved and the solution became hazy. The mixture was poured into a polyethylene bottle and polymerized at 50° C. for 22 hours. The product was worked up as usual, yielding 12.94 g of polymer having a Gardner viscosity of Z, corresponding to 59.24% conversion of monomer.

The sodium carboxylactamate activator can be made by an embodiment of this process in which the alcohol, removed from the reaction mixture of alkoxide and lactam, is subsequently reacted with metallic sodium to regenerate sodium alkoxide, and this alkoxide is recycled to the lactam reaction zone.

EXAMPLE 18

Sodium methoxide was made by adding to a solution of 96 g of methanol in 300 ml of dry benzene, 9.22 g of sodium metal, in small portions, under a nitrogen stream, over a period of 2 hours. The mixture was allowed to stand for 16 hours. It was then distilled until there was no methanol in the distillate. Benzene (364 ml) was added during distillation to replace the distillate. 37.45 g of purified 2-pyrrolidone was added to the sodium methoxide solution at reflux over a period of 19 minutes. The resulting mixture was distilled until the distillate was free of methanol. The solid product was filtered, washed with benzene and pentane, and dried in a vacuum desiccator. Yield: 43.01 g of sodium pyrrolidonate.

EXAMPLE 19

The procedure of Example 18 was repeated using 9.18 grams of sodium. The sodium pyrrolidonate product was not isolated, but after cooling the slurry to room temperature, 200 ml of benzene were added to make a total volume of 300 ml. Carbon dioxide was bubbled through the mixture for 25 minutes with the addition of 30 ml of benzene to facilitate stirring. The temperature rose from 27° to 38° C. The solid product was filtered, washed with benzene and pentane and dried in a vacuum desiccator yielding 50.63 g of a sodium carboxypyrrolidonate/sodium pyrrolidonate mixture.

EXAMPLE 20

The sodium carboxypyrrolidonate mixture of Example 19 was used to catalyze the polymerization of 2-pyrrolidone by mixing 22.5 g of purified 2-pyrrolidone with 3.4 g of the catalyst system of Example 19, heating the mixture to 100° C. for 15 minutes to effect dissolution, and polymerizing for 22 hours at 50° C. The polymeric product worked up as usual to give 12.41 g of polymer (corresponding to 52.1% conversion of monomer) having a Gardner viscosity of U-V.

Examples 21 and 22 show the use of potassium alkoxide-derived catalyst systems in the polymerization of 2-pyrrolidone.

EXAMPLE 21

200 g of purified 2-pyrrolidone was mixed with 26.52 g of potassium butoxide [$KOC(CH_3)_3$]. This mixture was heated to incipient distillation at 110° C./1.5 mm Hg and then sufficient carbon dioxide was added to the mixture to give a final $CO_2$ concentration of 3 mol percent. The mixture was polymerized for 22 hours at 50° C. The product was chopped up, washed, filtered and dried. The polymeric product had a viscosity on the Gardner Scale of U-V and it corresponded to 45% conversion of monomer.

EXAMPLE 22

50 g of purified 2-pyrrolidone was mixed with 19 ml of potassium methoxide in methanol (3 mM $KOCH_3$/ml) and after heating to incipient distillation of 95° C./1.5 mm Hg, carbon dioxide was added to the mixture. The mixture was polymerized for 22 hours at 50° C. The product was comminuted, washed, filtered and dried to yield 20.25 g of polymer, corresponding to 46.8% conversion of monomer, and having a viscosity on the Gardner Scale of W.

EXAMPLE 23

A series of pyrrolidone polymerizations were carried out in the presence of catalyst systems formed by adding less than a molar amount of carbon dioxide to a slurry of sodium pyrrolidonate in benzene derived from sodium methoxide. The resulting solid products were removed by filtration, washed with benzene and hexane, and dried. The catalyst systems prepared in this way were subjected to sodium and nitrogen analysis from which the sodium:carbon dioxide ratios were calculated. Each catalyst system was then used at 10 mol percent (based on total monomer) to effect 2-pyrrolidone polymerization at 50° C. for twenty-two hours. The results were as follows:

| $Na:CO_2$ Mol Ratio | % Monomer Conversion |
|---|---|
| 1:0.3 | 10% |
| 1:0.4 | 45–54% |
| 1:0.75 | 26% |
| 1:0.85 | 19% |

EVALUATION

Under polymerization conditions in which a polymerizate comprising about 10 mol percent of an alkaline catalyst derived from an alkali metal compound and about 3 mol percent of carbon dioxide, based on total monomer, is polymerized for about 22 hours at a temperature of about 50° C., satisfactory yields of polypyrrolidone are preferably those corresponding to at least about 40% or more conversion of monomer. A satisfactory catalyst system including an alkali metal carboxypyrrolidonate will produce satisfactory yields of polypyrrolidone under these conditions.

TABLE I
POLYMERIZATION OF PYRROLIDONE WITH POTASSIUM-DERIVED CATALYST SYSTEM[1]

| Example No. | Catalyst Preparation | Treatment Polymerizate | Conversion, % | Gardner Viscosity[2] |
|---|---|---|---|---|
| K metal-Derived | | | | |
| 3 | Isolated | None | 49.3 | X-Y |
| 4 | Isolated | Incipient Dist. | 55.4 | X-Y |
| 5 | Isolated | 24% of monomer distilled | 56.9 | X-Y |
| KOH-Derived | | | | |
| 1 | In Situ | Incipient Dist. | 48.9 | $Z_2$ |
| 2 | Isolated | Incipient Dist. | 53.3 | $Z_1$ |
| KOR-Derived | | | | |
| 21 | In Situ | Incipient Dist. | 45 | U-V |
| 22 | In Situ | Incipient Dist. | 46.8 | W |

[1]Catalyst system consisting of 10 mol percent potassium pyrrolidonate and 3 mol percent carbon dioxide, based on total 2-pyrrolidone.
[2]0.5 grams of polymer/10 ml of 90% HCOOH.

TABLE II
POLYMERIZATION OF PYRROLIDONE WITH SODIUM-DERIVED CATALYST SYSTEM[1]

| Example No. | Catalyst Preparation | Treatment of Polymerizate | Conversion, % | Gardner Viscosity[2] |
|---|---|---|---|---|
| Na metal-Derived | | | | |
| 7 | Isolated | None | 0.1 | |
| 8 | Isolated | Incipient Dist. | 4.2 | <A |
| 9 | Isolated | 16% of monomer distilled | 8.4 | <A |
| 10 | In Situ | None | 0.1 | |
| NaOH-Derived | | | | |
| 6 | In Situ | Incipient Dist. | 35.3 | U-V |

[1]Catalyst system consisting of 10 mol percent sodium pyrrolidonate and 3 mol percent carbon dioxide, based on total 2-pyrrolidone.
[2]0.5 grams of polymer/10 ml of 90% HCOOH.

TABLE III
POLYMERIZATION OF PYRROLIDONE WITH CARBOXYPYRROLIDONATE CATALYST SYSTEM

| Example No. | Catalyst Preparation | Catalyst Age, Days | Treatment of Polymerizate | Conversion, % | Gardner Viscosity[3] |
|---|---|---|---|---|---|
| NaOCH$_3$ Derived | | | | | |
| 12 | Isolated[1] | 1 | None | 40.8 | X-Y |
| 14 | Isolated[1] | 7 | None | 39.6 | Y |
| 16 | Isolated[1] | 15 | None | 53.8 | Y-Z |
| 13 | Isolated[1] | 1 | Heated to incipient dist. | 60.3 | X-Y |
| 15 | Isolated[1] | 7 | Heated to incipient dist. | 60.3 | Y-Z |
| 17 | Isolated[1] | 15 | Heated to 100° C. to dissolve catalyst. | 59.2 | Z |
| KOH-Derived | | | | | |

TABLE III-continued
POLYMERIZATION OF PYRROLIDONE WITH CARBOXYPYRROLIDONATE CATALYST SYSTEM

| Example No. | Catalyst Preparation | Catalyst Age, Days | Treatment of Polymerizate | Conversion, % | Gardner Viscosity[3] |
|---|---|---|---|---|---|
| 1 | In Situ[2] | — | Heated to incipient dist. | 48.9 | X-Y |
| NaOH-Derived | | | | | |
| 6 | In Situ[2] | — | Heated to incipient dist. | 35.3 | U-V |

[1]Catalyst system consisting of 10 mol percent sodium pyrrolidonate and 5 mol percent carbon dioxide, based on total 2-pyrrolidone.
[2]Catalyst system consisting of 10 mol percent potassium (sodium) pyrrolidonate and 3 mol percent carbon dioxide, based on total 2-pyrrolidone.
[3]0.5 grams of polymer/10 ml of 90% HCOOH.

The examples are summarized in Tables I–III. Table I illustrates the satisfactory polymerization results obtained from potassium-derived catalyst systems containing potassium carboxypyrrolidonate, while Table II illustrates the comparatively unsatisfactory polymerization results obtained from various sodium-derived catalyst systems containing sodium carboxypyrrolidonate under substantially identical polymerization conditions and polymerizate treatments as in the potassium-derived catalyst polymerizations. Table III illustrates the unexpectedly satisfactory polymerization results obtainable from a catalyst system comprising a sodium carboxypyrrolidonate derived from a sodium alkoxide according to the process of the present invention.

Example 6 of Table II and Example 1 of Table I are directly comparable and show the unsatisfactorily lower yield one obtains from sodium hydroxide-derived catalyst systems containing sodium carboxypyrrolidonate than from potassium hydroxide-derived catalyst systems containing potassium carboxypyrrolidonate under the same conditions of polymerization and polymerizate treatment.

Comparison of Examples 7–9 of Table II to Examples 3–5 of Table I shows the sharp contrast in polymer product yields and polymer product viscosity between metallic sodium-derived catalyst systems and metallic potassium-derived catalyst systems each containing carboxypyrrolidonate of the corresponding alkali metal.

In an unexpected exception to the generally unsatisfactory, or poorer, polymerization results obtained from sodium-derived catalyst systems containing sodium carboxylactamate, it was found that a catalyst system containing a sodium carboxylactamate derived from a $C_1$–$C_5$ sodium alkoxide by the process described herein is capable of producing unexpectedly higher and very satisfactory yields of polypyrrolidone of X-Z viscosity. This catalyst system is easily purified and does not lose its catalytic effectiveness with time. These results are illustrated in Table III wherein percent conversion of monomer under catalytic activation by this sodium carboxypyrrolidonate range from 40 to 60% under conditions of polymerization and polymerizate treatment which are substantially identical to those of Table I and II.

What is claimed is:

1. A process for the preparation of an isolatable alkaline catalyst for the polymerization of 2-pyrrolidone, whereby said catalyst retains its catalytic activity for a period of at least 15 days, comprising the steps of forming a sodium lactamate precipitate by heating at about reflux temperature a $C_1$–$C_5$ sodium alkoxide with about a stoichiometrically equivalent amount of a 5–7 membered-ring lactam and an inert liquid nonsolvent for said sodium lactamate, thereby forming a slurry of said sodium lactamate precipitate dispersed in said inert liquid nonsolvent, contacting said sodium lactamate precipitate in said slurry with carbon dioxide, and recovering the resulting product.

2. A process according to claim 1 wherein said sodium alkoxide is sodium methoxide, said 5–7 membered-ring is 2-pyrrolidone and said inert liquid non-solvent is benzene.

* * * * *